US009238148B2

(12) United States Patent
Ananth

(10) Patent No.: US 9,238,148 B2
(45) Date of Patent: Jan. 19, 2016

(54) METHOD FOR INCREASING BUCK REGULATOR EFFICIENCY USING CHARGE RECAPTURING IN AN IMPLANTABLE CARDIAC DEVICE

(71) Applicant: Cameron Health, Inc., San Clemente, CA (US)

(72) Inventor: Ravi S. Ananth, Laguna Niguel, CA (US)

(73) Assignee: CAMERON HEALTH, INC., St. Paul, MN (US)

( * ) Notice: Subject to any disclaimer, the term of this patent is extended or adjusted under 35 U.S.C. 154(b) by 292 days.

(21) Appl. No.: 13/938,473

(22) Filed: Jul. 10, 2013

(65) Prior Publication Data

US 2015/0018756 A1    Jan. 15, 2015

(51) Int. Cl.
*A61N 1/08* (2006.01)
*A61N 1/39* (2006.01)
*A61M 5/172* (2006.01)
*A61M 1/10* (2006.01)
*A61M 5/142* (2006.01)

(52) U.S. Cl.
CPC ............ *A61N 1/3975* (2013.01); *A61N 1/3956* (2013.01); *A61N 1/3981* (2013.01); *A61M 1/1086* (2013.01); *A61M 5/14276* (2013.01); *A61M 5/1723* (2013.01); *A61M 2005/1726* (2013.01); *A61M 2205/8212* (2013.01)

(58) Field of Classification Search
CPC ........... A61N 1/36128; A61N 1/36146; A61N 1/36153; A61N 1/36189; A61N 1/3782; A61N 1/3975; A61N 1/3956; A61N 1/3981; A61M 5/1723
USPC ............................................. 607/5, 7, 11, 12
See application file for complete search history.

(56) References Cited

U.S. PATENT DOCUMENTS

| 5,994,885 | A | 11/1999 | Wilcox et al. |
| 6,380,722 | B2 | 4/2002 | Wickersham |
| 6,639,388 | B2 | 10/2003 | Tihanyi |
| 6,647,292 | B1 | 11/2003 | Bardy et al. |
| 7,734,343 | B2 | 6/2010 | Ransbury et al. |
| 2010/0324616 | A1* | 12/2010 | Livnat et al. ...................... 607/6 |
| 2012/0277830 | A1* | 11/2012 | Arfin et al. ......... A61N 1/36146 607/62 |
| 2013/0035735 | A1 | 2/2013 | Kroll |

* cited by examiner

*Primary Examiner* — Theodore Stigell
*Assistant Examiner* — Michael Carey
(74) *Attorney, Agent, or Firm* — Seager, Tufte & Wickhem LLP

(57) ABSTRACT

A typical power switch in a Buck Regulator requires a pre-driver to ensure rapid transition from its ON to OFF states. In this invention, the shoot through current in the pre-driver and the power switch's gate-charge in a Buck regulator is itself recaptured in the capacitor of the buck regulator. The recapturing of this otherwise wasted shoot-through current and gate charge allows for increased efficiency of the regulator. The recapture may be selectively disabled to accommodate high power operations of the system, if such are used; the recapture may in an alternative mode be always performed. As a result, reduced power consumption can be achieved.

17 Claims, 3 Drawing Sheets

METHOD FOR INCREASING BUCK REGULATOR EFFICIENCY USING CHARGE RECAPTURING IN AN IMPLANTABLE CARDIAC DEVICE

BACKGROUND

A buck regulator is a circuit that generates a power supply that is at a lower voltage than the higher voltage power source from which it is derived. It improves the efficiency of an overall system, by delivering the current needed by a system from a lower voltage supply than the power source voltage itself. The main components of a buck regulator are a switch, a switch control circuit, an inductor, a diode and a capacitor. The switch is connected to the higher voltage power source and the duty cycle of the switch determines the fraction of the original power supply voltage that will be supplied by the buck regulator.

FIG. 1 illustrates a prior art version of a typical buck regulator. The pre-drivers shown at 16, 18 and 20 in FIG. 1 are needed to drive the final switch at 26 due to the typically large size of the switching device. The switch at 26 couples and decouples a power supply (shown as a battery) 28 to an inductor L 30. The inductor 30 is coupled to a capacitor C1 32 and a load Z 34. This provides an output Vout 36 as shown. A diode 38 is used to conduct the charging current during the time the switch is initially turned off and completes the loop. While switch 26 is closed, energy is transferred from the power supply 28 to the inductor 30 and capacitor 32. When switch 26 is open, current stored in the inductor flows through the loop created by the inductor 30, diode 38 and the parallel structure of the capacitor 32 and load 34. If desired, load 34 may be depicted separately from the rest of the circuit.

One issue with this solution is that the pre-driver inverters 16, 18, and 20 consume and hence waste power due to the shoot-through current that passes through them to ground as they switch between ON and OFF states. The charge on the gate-capacitance of the switch, 26, also wastes power as it is charged and discharged during every switching cycle. One goal of the present invention is to provide an alternative solution to increase efficiency by reducing the above wastage.

OVERVIEW

The Inventor has recognized that the shoot through current in the pre-drivers of a Buck-regulator switch as well as the charge on the switch's gate-capacitance may be reused in the same buck regulator circuit, if certain conditions are met. As a result, significant improvements in Buck regulator efficiency can be made. The charge capturing method can be activated as necessary to ensure that sufficient gate-to-source voltage exists on the switch under all conditions. When the voltage of the power source such as a battery is lowered due to high current draw or drop across a battery's equivalent series resistor (ESR), it may not be advisable to recapture shoot through current or gate-capacitance charge. Such a condition is generally infrequent and hence, the current and charge re-capturing method can be used for the majority of the time to improve regulator efficiency.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives.

Figure 1:
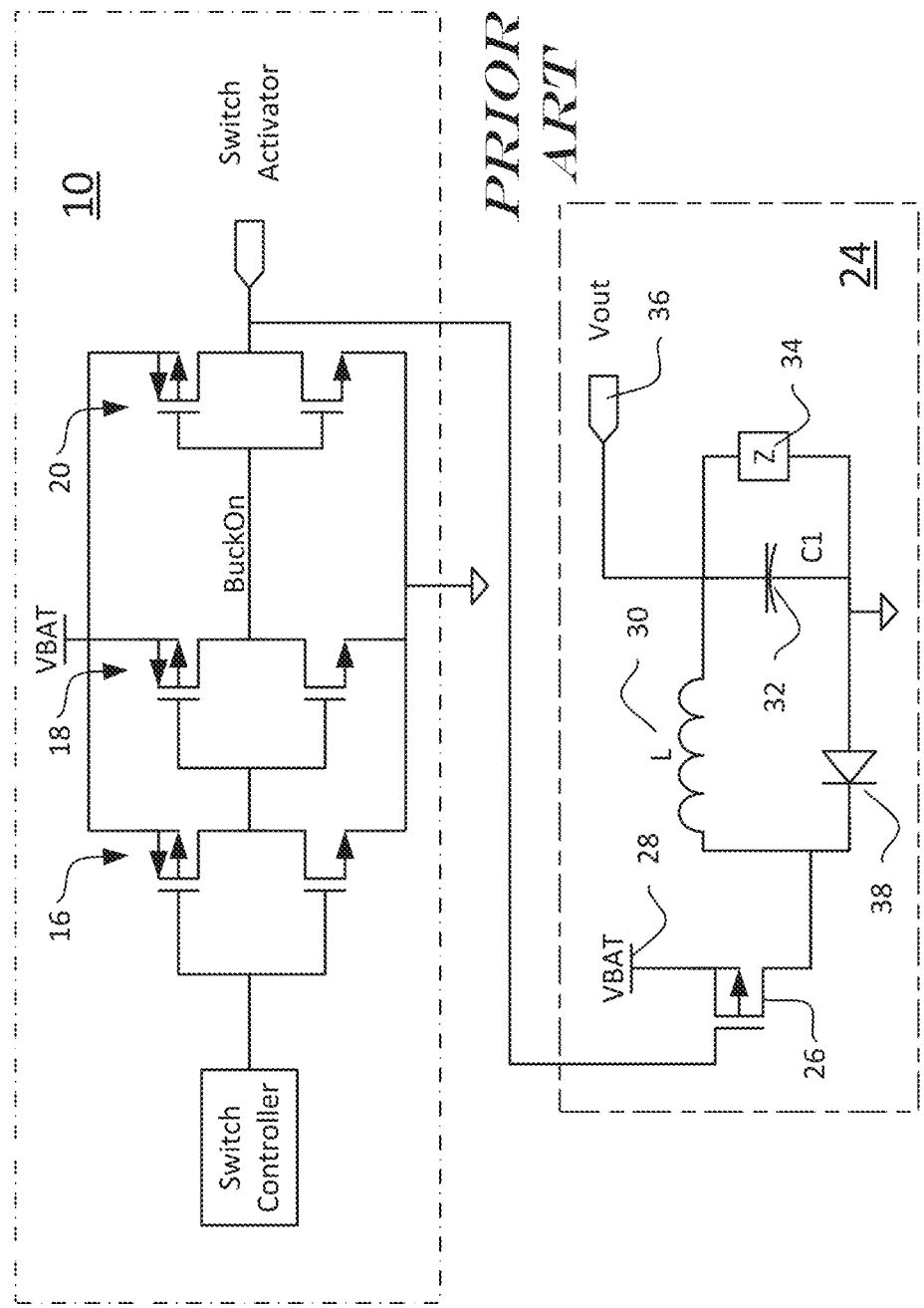
FIG. 1 shows a schematic for a prior art buck regulator.
Figure 2:
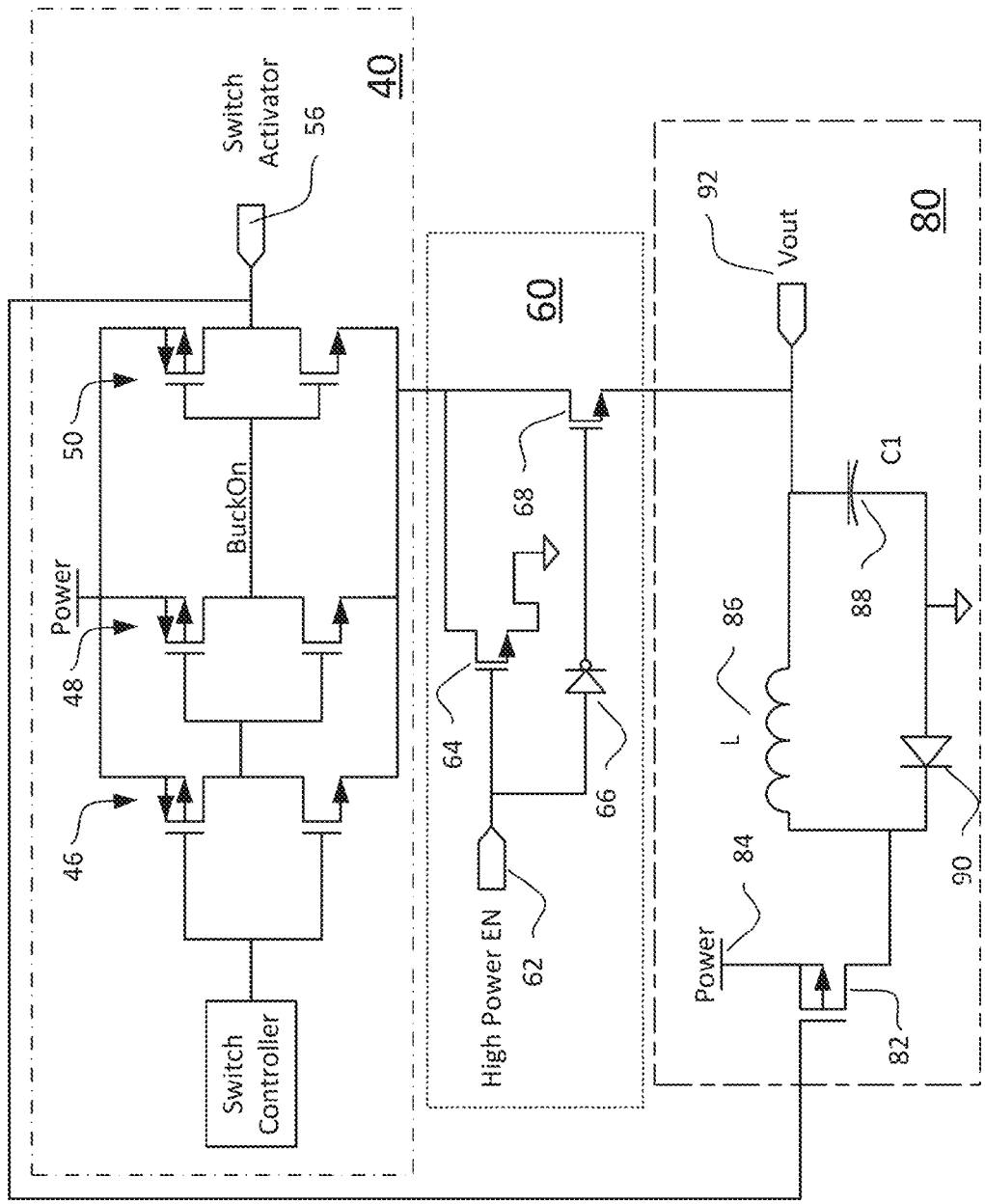
FIG. 2 illustrates a buck regulator capable of recapturing shoot-through current for use in generation of the output reference voltage.

FIG. 1 shows a schematic for a prior art buck regulator and is described above in the Background section. FIG. 2 illustrates a buck regulator capable of recapturing shoot-through current and switch gate-charge for use in the generation of the output supply voltage and is representative of several embodiments of the present invention.

In FIG. 2, the switch controller and pre-drivers are shown again shown at 40 and is generally the same as previously described. The buck regulator 80 is largely the same, with a switch 82 controlled by the switch activator 56, that makes the switch connect and disconnect the power source 84 to the inductor 86. The diode 88 allows for the stored current in the inductor to charge the output capacitor 88 when the switch is turned off. The resulting stored charge results in the output supply voltage, Vout at 92.

The new element in FIG. 2 is the inclusion of a pre-driver shoot-through current and switch gate-charge capture circuit depicted at 60. In the example shown a control input 62 (explained later) is coupled to a first switch 64 and, via an inverter 66, to a second switch 68. When the control input 62 is ON, switch 64 is closed and the shoot-through current from the pre-drivers 46, 48 and 50 and the switch's gate-charge is directed to ground and therefore lost. If the control input is OFF, switch 64 is opened, while inverter 66 provides an ON input to switch 68, directing shoot-through current from the pre-drivers 46, 48 and 50 along with the gate-charge on the switch 82 to capacitor 88. Thus, when switch 68 is closed, the shoot-through current and gate-charge on the switch 82 are used to assist with the supply voltage generation thereby increasing the buck-regulator's efficiency. This results in less current used by the overall system.

For the shoot-through current and charge recapture circuit to work well, the Vout 92 has to be small relative to the Power input to the system, to allow sufficient over-drive voltage to the switch 82 if the switch 82 is a PFET. If the voltage of the Power source is pulled down due to voltage drops across the source's equivalent series resistance (ESR) or due to excessive current draw by the system, then the over-drive voltage on the switch (assuming it is a PFET) will be reduced. As a result, the shoot-through current and charge recapture circuit operation may be compromised. Therefore, in this example, the switch at 64 is controlled by a "High Power EN" signal. When the high power circuitry in the device is in an "ON" state, the High Power EN signal 62 goes high, sending the shoot-through current directly to ground and ensuring that adequate over-drive voltage is available for the switch 82 to operate efficiently (again assuming switch 82 is a PFET).

For example, this circuit may be used in an implantable medical device such as an implantable cardiac defibrillator that provides high energy outputs such as defibrillation therapy. To provide such high energy outputs in a timely fashion, the battery will be taxed heavily for short periods of time. Therefore the "High Power EN" signal is used to disable the use of the shoot through capture circuit when the battery is potentially being used for high power operations. In another example, the charge capture circuit 60 may be an always-on circuit, which can eliminate elements 62, 64, 66 and 68 and simply directs the current through to the capacitor 88 always.

Figure 3:
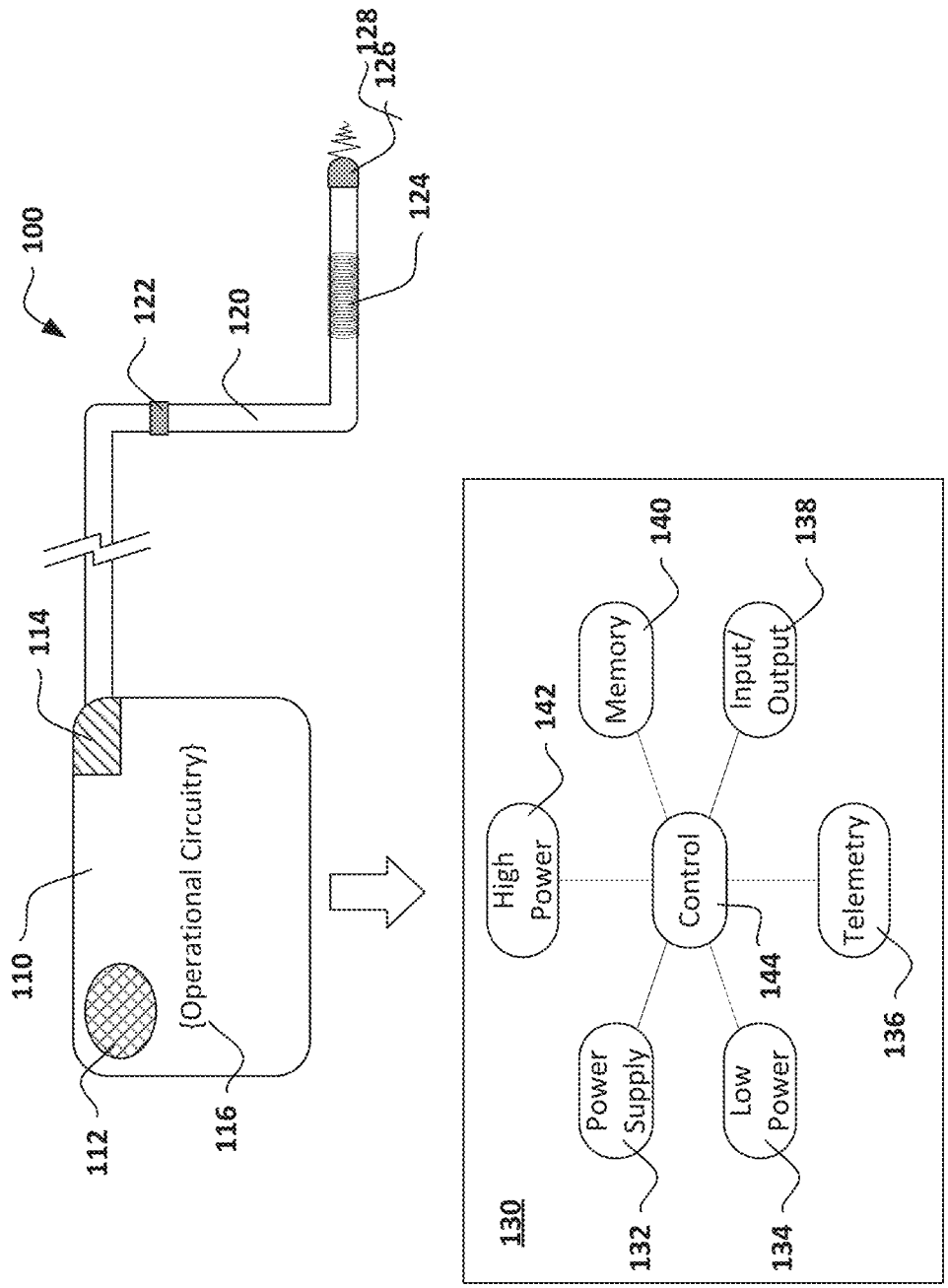
FIG. 3 illustrates an implantable medical device.

FIG. 3 illustrates an implantable medical device in which the present invention may be used. The device is illustrated at 100 and includes a canister 110 and lead 120. Some illustrative features may include, for example, an electrode 112 on the canister 110 and a header 114 for coupling with the lead 120. The electrode 112 may be integral with the canister 110 or it may actually be the outer shell of the canister 110. The canister 110 will typically be a hermetically sealed unit that houses operational circuitry 116 for the implantable system 100.

The operational circuitry 116 may include various elements, and some illustrations are provided at 130. Typically, there will be a power supply 132, usually having one or more batteries which may or may not be rechargeable. For example, many cardiac stimulation devices have non-rechargeable batteries, although some implantable devices are instead rechargeable. There is usually some amount of low-power and mid-power circuitry 134 that can drive various functions including logic and processing, telemetry circuitry 136 with an RF radio, inductive telemetry or other technical solution (sonic, infrared) for communicating with a non-implanted external programmer, network or other device, input/output circuitry 138 for receiving, amplifying, filtering, etc. a biological signal or delivering electrical stimulus, for example, or powering a drug dispensing apparatus for drug delivery in a drug pump, etc., memory 140 for storing instructions for operation as well as records of activity, observed events, treatment, status logs, etc. In addition, some devices include high power circuitry 142 such as the output circuitry for an implantable cardiac defibrillator. All of these elements 132-142 typically couple with one another via a control module 144 which may include a controller or processor.

The provision of each of a canister 110, with electrode 112 and header 114, and lead 120 with electrodes 122, 124, 126 and a distal attachment feature 128, as shown in FIG. 3 is merely illustrative. Other designs can also be used; for example, some implantable cardiac monitoring devices and/or so-called "seed" pacemakers have only a canister 110 and omit a lead 120. Some proposed systems include an elongated flexible housing (i.e. U.S. Pat. No. 6,647,292 (unitary subcutaneous defibrillator) or U.S. Pat. No. 7,734,343 (intravascular active medical implant) for example).

The various elements shown at 130 are not all required in any one system. For example, a device may use conducted emissions for communication, provided through the input/output circuitry 138 and omit the telemetry circuit 136 entirely. A lower power stimulus device may omit the high power circuit 142. A rechargeable device may include a recharge circuit (not shown) coupled to the power supply. Output circuits and high power circuitry 142 may be left out of an implantable loop recorder. The low power circuit 134 and control circuitry 144 may be combined. The indication that elements couple via control circuitry 144 is merely illustrated; in some instances the outer elements 132-142 may be directly connected together with control circuitry 144 simply controlling operation, rather than routing connections.

Referring back to FIG. 2, the following particular non-limiting examples are disclosed:

Example 1 is an implantable cardiac device comprising a battery (where "Power" 84 is the battery or is generated from a battery), a high power circuit for therapy delivery having an enabling input (high power EN 62) which determines whether the high power circuit is active or inactive, a control circuit that provides the enabling input 62 to the high power circuit, and a buck-regulator based power supply having a buck oscillator 40 and a resonant circuit 80 controlled in a duty cycled manner by the buck oscillator, the resonant circuit 80 including a maintaining capacitor 88 for maintaining a reference voltage for use as an output 92 from the buck regulator. In Example 1, the improvement comprises a shoot-through current capture circuit 60 coupled to the buck oscillator 40, an internal ground of the medical device, the enabling input 62 for the high power circuit, and the maintaining capacitor 88 such that: when the enabling input 62 is set to render the high power circuit active, the shoot through capture circuit 60 directs a shoot-through current from the buck oscillator 40 to ground (e.g. via switch 64); or when the enabling input 62 is set to render the high power circuit inactive, the shoot through capture circuit 60 directs the shoot-through current from the buck oscillator 40 to the maintaining capacitor 88. By routing shoot through current in this way, the system also recaptures charge from a switch 82 used to control the resonant circuit 80.

Example 2 is based on Example 1 and is further configured such that the buck oscillator 40 comprises at least one pre-driver 46, 48, 50 that provides a low output or a high output in response to an input signal which generates the shoot-through current as it switches from a high to a low output.

Example 3 is based on Example 1 and is further configured such that the at least one pre-driver 46, 48, 50 of the buck oscillator 40 is powered directly from the battery.

Example 4 is based on Example 1 and is further configured such that resonant circuit 80 of the buck regulator based power supply also includes an inductor 86 and a diode 90 such that the maintaining capacitor 88, inductor 86 and diode 90 are coupled together in a loop.

Example 5 takes the form of an implantable medical device comprising a battery, in which power 84 is a battery or is generated by a battery, and a buck-regulator based power supply having a buck oscillator 40 and a resonant circuit 80 controlled in a duty cycled manner by the buck oscillator 40, the resonant circuit 80 including a maintaining capacitor 88 for maintaining a reference voltage for use as an output from the buck regulator, and the buck oscillator 40 includes at least one pre-driver 46, 48, 50 that generates a shoot-through current upon switching from a first output to a second output, in which the improvement is a shoot-through current capture circuit 60 coupled to the buck oscillator circuit 40 to capture shoot through current and direct the shoot through current to the maintaining capacitor 88.

Example 6 is based example 5 and is further configured such that the at least one pre-driver 46, 48, 50 of the buck oscillator 40 is powered directly from the battery.

Example 7 is based on example 5 and is further configured such that the resonant circuit 80 of the buck regulator based power supply also includes an inductor 86 and a diode 90 such that the maintaining capacitor 88, inductor 86 and diode 90 are coupled together in a loop.

Example 8 takes the form of a method of operating circuitry inside of a battery powered implantable cardiac device comprising using an oscillator 40 to generate a time changing output, the oscillator including at least one pre-driver 46, 48, 50 that switches from a high output to a low output periodically to aid in generation of the time changing output, wherein the at least one pre-driver 46, 48, 50 creates a shoot-through current upon switching from one output to the other. Example 8 further includes using the time changing output to drive a buck regulator circuit 80 comprising an output-maintaining capacitor 88 to hold a buck regulator output voltage, and providing the shoot-through current to the output-maintaining capacitor 88 to improve the efficiency of the device.

Example 9 is a method based on example 8 and is performed such that the battery powered device comprises high voltage circuitry for generating a voltage that exceeds a voltage of a battery that powers the battery powered device; the high voltage circuitry is configured to be selectively enabled; and the step of providing the shoot through current to the output-maintaining capacitor 88 is performed only when the high voltage circuitry is not enabled.

Example 10 is an alternative to Example 9 and again is a method based on example 8, in which the step of providing the shoot-through current to the output-maintaining capacitor 88 is always performed.

Each of these non-limiting examples can stand on its own, or can be combined in various permutations or combinations with one or more of the other examples.

In a working example, the following values are used: L=47 μH at 86, C1=47 μF at 88, with the Switch Controller set to generate a 2.35V output voltage from a power input 84 in the range of about 8.5 to 9.5 volts. The working example illustrated current savings while providing a stable output during periods of High Power 62 ON and High Power 62 OFF.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations.

The scope of the invention should be determined with reference to the appended claims, along with the full scope of equivalents to which such claims are entitled.

The claimed invention is:

1. An implantable cardiac device comprising:
   a battery;
   a high power circuit for therapy delivery having an enabling input which determines whether the high power circuit is active or inactive;
   a control circuit that provides the enabling input to the high power circuit; and
   a buck-regulator based power supply having a buck oscillator and a resonant circuit controlled in a duty cycled manner by the buck oscillator, the resonant circuit including a maintaining capacitor for maintaining a reference voltage for use as an output from the buck regulator;
   the improvement comprising a shoot-through current and switch gate-charge re-capture circuit coupled to the buck oscillator, an internal ground of the medical device, the enabling input for the high power circuit, and the maintaining capacitor such that: when the enabling input is set to render the high power circuit active, the shoot through capture circuit directs a shoot-through current from the buck oscillator to ground; or
   when the enabling input is set to render the high power circuit inactive, the shoot through capture circuit directs the shoot-through current and switch gate-charge from the buck oscillator to the maintaining capacitor.

2. The implantable cardiac device of claim 1 wherein the buck oscillator comprises at least pre-driver that provides a low output or a high output in response to an input signal which generates the shoot-through current as it switches from a high to a low output.

3. The implantable cardiac device of claim 2 wherein the at least one pre-driver of the buck oscillator is powered directly from the battery.

4. The implantable cardiac device of claim 1 wherein the resonant circuit of the buck regulator based power supply also includes an inductor and a diode such that the maintaining capacitor, inductor and diode are coupled together in a loop.

5. The implantable cardiac device of claim 1 wherein the device comprises electrodes for sensing a biological signal and output circuitry for delivering a high power defibrillation therapy such that the device is an implantable defibrillator.

6. The implantable cardiac device of claim 1 wherein the device comprises electrodes for sensing a biological signal and a drug dispensing output for delivering a drug to a patient in response to identified conditions such that the device is an implantable drug pump.

7. The implantable cardiac device of claim 1 wherein the device comprises electrodes for sensing biological signals and circuitry for receiving power to recharge the battery.

8. An implantable cardiac device comprising:
a battery; and
a buck-regulator based power supply having a buck oscillator and a resonant circuit controlled in a duty cycled manner by the buck oscillator, the resonant circuit including a maintaining capacitor for maintaining a reference voltage for use as an output from the buck regulator, and the buck oscillator includes at least one pre-driver that generates a shoot-through current upon switching from a first output to a second output;
the improvement comprising a shoot-through current capture circuit coupled to the buck oscillator circuit to capture shoot through current and direct the shoot through current to the maintaining capacitor.

9. The implantable cardiac device of claim 8 wherein the at least one pre-driver circuit of the buck oscillator is powered directly from the battery.

10. The implantable cardiac device of claim 8 wherein the resonant circuit of the buck regulator based power supply also includes an inductor and a diode such that the maintaining capacitor, inductor and diode are coupled together in a loop.

11. The implantable cardiac device of claim 1 wherein the device comprises electrodes for sensing a biological signal and output circuitry for delivering a high power defibrillation therapy such that the device is an implantable defibrillator.

12. The implantable cardiac device of claim 1 wherein the device comprises electrodes for sensing a biological signal and a drug dispensing output for delivering a drug to a patient in response to identified conditions such that the device is an implantable drug pump.

13. The implantable cardiac device of claim 1 wherein the device comprises electrodes for sensing biological signals and circuitry for receiving power to recharge the battery.

14. A method of operating circuitry inside of a battery powered implantable cardiac device comprising:
using an oscillator to generate a time changing output, the oscillator including at least one pre-driver that switches from a high output to a low output periodically to aid in generation of the time changing output, wherein the at least one pre-driver creates a shoot-through current upon switching from one output to the other;
using the time changing output to drive a buck regulator circuit comprising an output-maintaining capacitor to hold a buck regulator output voltage; and
providing the shoot-through current to the output-maintaining capacitor to improve the efficiency of the device.

15. The method of claim 14 wherein: the battery powered device comprises high voltage circuitry for generating a voltage that exceeds a voltage of a battery that powers the battery powered device; the high voltage circuitry is configured to be selectively enabled; the step of providing the shoot through current to the output-maintaining capacitor is performed only when the high voltage circuitry is not enabled.

16. The method of claim 15 further comprising charging a high voltage capacitor designed for defibrillation therapy delivery when the high voltage circuitry is enabled.

17. The method of claim 14 wherein the step of providing the shoot-through current to the output-maintaining capacitor is always performed.

* * * * *